US008835666B2

(12) United States Patent
Brazdil, Jr. et al.

(10) Patent No.: US 8,835,666 B2
(45) Date of Patent: Sep. 16, 2014

(54) PRE CALCINATION ADDITIVES FOR MIXED METAL OXIDE AMMOXIDATION CATALYSTS

(71) Applicant: Ineos USA LLC, Lisle, IL (US)

(72) Inventors: James Frank Brazdil, Jr., Glen Ellyn, IL (US); Charles James Besecker, Naperville, IL (US); Michael J. Seely, Plainfield, IL (US); Muin S. Haddad, Naperville, IL (US); Mark A. Toft, Somonauk, IL (US)

(73) Assignee: Ineos USA LLC, Lisle, IL (US)

( * ) Notice: Subject to any disclaimer, the term of this patent is extended or adjusted under 35 U.S.C. 154(b) by 0 days.

(21) Appl. No.: 13/685,180

(22) Filed: Nov. 26, 2012

(65) Prior Publication Data

US 2014/0148610 A1 May 29, 2014

(51) Int. Cl.
  *B01J 23/887* (2006.01)
  *C07C 211/62* (2006.01)
  *C07C 205/06* (2006.01)
  *C07C 275/00* (2006.01)

(52) U.S. Cl.
  CPC .................................. *B01J 23/8878* (2013.01)
  USPC ........ 558/324; 502/249; 568/479; 562/512.2; 564/63; 564/284; 564/281

(58) Field of Classification Search
  USPC ....................................................... 558/324
  See application file for complete search history.

(56) References Cited

U.S. PATENT DOCUMENTS

| | | | |
|---|---|---|---|
| 3,892,794 A * | 7/1975 | Grasselli et al. ............... | 558/323 |
| 4,874,738 A * | 10/1989 | Brazdil et al. ................. | 502/209 |
| 5,093,299 A | 3/1992 | Suresh et al. | |
| 5,128,114 A | 7/1992 | Schwartz | |
| 5,212,137 A | 5/1993 | Suresh et al. | |
| 5,258,543 A * | 11/1993 | Suresh et al. ................. | 558/325 |
| 5,658,842 A | 8/1997 | Midorikawa et al. | |
| 5,834,394 A | 11/1998 | Chen et al. | |
| 6,914,029 B2 * | 7/2005 | Davis et al. .................... | 502/150 |
| 6,943,135 B2 | 9/2005 | Gaffney et al. | |
| 7,288,669 B2 | 10/2007 | Gaffney et al. | |
| 7,365,041 B2 | 4/2008 | Miyaki et al. | |
| 7,473,666 B2 | 1/2009 | Yanagi et al. | |
| 7,807,600 B2 | 10/2010 | Watanabe et al. | |
| 7,902,112 B2 * | 3/2011 | Yanagita et al. ............... | 502/241 |
| 8,153,546 B2 | 4/2012 | Bradzil et al. | |
| 8,258,073 B2 | 9/2012 | Besecker et al. | |
| 2005/0209479 A1 * | 9/2005 | Brazdil et al. ................. | 558/322 |
| 2006/0194693 A1 | 8/2006 | Watanabe et al. | |
| 2006/0248733 A1 | 11/2006 | Masai et al. | |
| 2011/0237753 A1 * | 9/2011 | Brazdil et al. ................. | 525/378 |
| 2011/0237820 A1 * | 9/2011 | Besecker et al. ............... | 558/321 |

FOREIGN PATENT DOCUMENTS

| | | | | |
|---|---|---|---|---|
| CN | 1393285 | A | * | 1/2003 |
| CN | 101147869 | A | | 3/2008 |
| CN | 101306372 | A | * | 11/2008 |
| JP | 2006061888 | A | | 3/2006 |
| JP | 2006263715 | A | | 10/2006 |
| JP | 2006326440 | A | | 12/2006 |
| JP | 2008/237963 | | * | 10/2008 |
| WO | WO2008050767 | A1 | | 5/2008 |

OTHER PUBLICATIONS

Jiang et al. "Preparation and uses of metal oxide ammoxidation catalyst," CN1393285A—Mahcine Translation (English), published Jan. 29, 2003.*
Zheng et al. "Effect of Preparation Condition on the Performance of MoVTeNbO Catalyst Materials for Selective Oxidation of Propane into Acrylic Acid" The Open Mater. Sci. J. 2008, 2, 23-27.*
Romanski et al. "Dry catalyst impregnation in a double cone blender: A computational and experimental analysis," Powder Technology, vol. 221, May 2012, pp. 57-69.*
Yanagida et al. "Manufacturing method of the catalyst for acrylonitrile synthesis" JP2008/237963—Machine Translation (English), published Oct. 9, 2008.*
Tao et al. "Fluidized-bed catalyst for production of acrylonitrile from ammoxidation of propylene." CN 101306372 A—Machine Translation(English), published Nov. 19, 2008.*

* cited by examiner

*Primary Examiner* — Samantha Shterengarts
*Assistant Examiner* — Amanda L Aguirre
(74) *Attorney, Agent, or Firm* — Ineos USA LLC

(57) ABSTRACT

A process for preparation of catalysts for the production of acrylonitrile, acetonitrile and hydrogen cyanide comprising contacting at an elevated temperature, propylene, ammonia and oxygen in the vapor phase in the presence of a catalyst, said catalyst comprising a complex of metal oxides wherein a heat-decomposable nitrogen containing compound is added during the process for the preparation of the catalyst.

15 Claims, No Drawings

PRE CALCINATION ADDITIVES FOR MIXED METAL OXIDE AMMOXIDATION CATALYSTS

BACKGROUND OF THE INVENTION

1. Field of the Invention

The present invention relates to an improved catalyst for use in the ammoxidation of an unsaturated hydrocarbon to the corresponding unsaturated nitrile. In particular, the present invention is directed to the process for making an improved catalyst for the ammoxidation of propylene and/or isobutylene to acrylonitrile and/or methacrylonitrile, respectively and the oxidation of propylene and/or isobutylene to acrolein/ acrylic acid and/or methacrolein/methacrylic acid, respectively. More specifically, the invention relates to the process for producing an improved multi-component ammoxidation catalyst comprising a complex of metal oxides wherein a heat-decomposable nitrogen containing compound is added during the process for the preparation of the catalyst prior to the calcination of the catalyst.

2. Description of the Prior Art

Catalysts containing oxides of iron, bismuth and molybdenum, promoted with suitable elements, have long been used for the conversion of propylene and/or isobutylene at elevated temperatures in the presence of ammonia and oxygen (usually in the form of air) to manufacture acrylonitrile and/or methacrylonitrile. In particular, Great Britain Patent 1436475; U.S. Pat. Nos. 4,766,232; 4,377,534; 4,040,978; 4,168,246; 5,223,469 and 4,863,891 are each directed to bismuth-molybdenum-iron catalysts which may be promoted with the Group II elements to produce acrylonitrile. In addition, U.S. Pat. Nos. 5,093,299, 5,212,137, 5,658,842 and 5,834,394 are directed to bismuth-molybdenum promoted catalysts exhibiting high yields to acrylonitrile.

In part, the instant invention relates to the preparation of bismuth-molybdenum-iron catalysts and the use of an additive as part of the preparation. Typically, such catalysts are produced in a batch process by simply combining and reacting, source compounds for the various metal components. However, more complex and multiple-step preparations have been used. For example, U.S. Pat. No. 4,040,978 taught a process for catalyst preparation where molybdates of each metal were separately made and then combined and reacted; and U.S. Pat. No. 4,148,757 taught a process for catalyst preparation where bismuth and molybdenum were first reacted to form a bismuth molybdate and then the bismuth molybdate was combined with a mixture of source compounds for the various other metal components.

Other than the addition of promoter elements and the use of various support materials, such as silica, the addition of additives to promote iron bismuth molybdate ammoxidation catalysts is atypical. This is less true with other catalyst systems. For example, U.S. Pat. No. 5,128,114 teaches the addition of ammonium citrate or urea to an aqueous silica sol, drying the mixture, and then calcining the dried powder to remove volatile components. The use of the additive produces attrition resistant microspheroidal particles. U.S. Pat. No. 5,128,114 describes using this method to prepare palladium and platinum-palladium catalysts supported on silica suitable as catalysts for the production of hydrogen peroxide by reaction of hydrogen and oxygen. U.S. Pat. No. 7,288,669 and U.S. Pat. No. 6,943,135 teach adding a source of $NO_x$ to the other ingredients employed in the catalyst preparation for catalysts for propane oxidation to acrylic acid or propane ammoxidation to acrylonitrile (Mo—V—Te—Nb—O type catalyst systems are exemplified).

SUMMARY OF THE INVENTION

The present invention is directed to an improved mixed metal oxide catalyst for the ammoxidation of propylene and/ or isobutylene. This improved catalyst, prepared as described herein, provides greater overall conversion of the propylene and/or isobutylene to nitriles (i.e. compounds having the function group "—CN", such as acrylonitrile, methacrylonitrile, acetonitrile and hydrogen cyanide), higher hydrogen cyanide production, and greater ammonia utilization efficiency. The present invention is also directed to an improved mixed metal oxide catalyst for the oxidation of propylene and/or isobutylene.

In one embodiment, the invention is directed to a process for the preparation a catalyst comprising a complex of metal oxides wherein the relative ratios of the elements in said catalyst are represented by the following formula:

$$Mo_{12}Bi_aFe_bA_cD_dE_eF_fG_gCe_hO_x$$

wherein A is at least one element selected from the group consisting of sodium, potassium, rubidium and cesium; and D is at least one element selected from the group consisting of nickel, cobalt, manganese, zinc, magnesium, calcium, strontium, cadmium and barium;

E is at least one element selected from the group consisting of chromium, tungsten, boron, aluminum, gallium, indium, phosphorus, arsenic, and vanadium;

F is at least one element selected from the group consisting of lanthanum, praseodymium, neodymium, samarium, europium, gadolinium, terbium, dysprosium, holmium, erbium thulium, ytterbium, lutetium, scandium, yttrium, titanium, zirconium, hafnium, niobium, tantalum, aluminum, gallium, indium, thallium, silicon, germanium, and lead;

G is at least one element selected from the group consisting of silver, gold, ruthenium, rhodium, palladium, osmium, iridium, platinum and mercury; and a is from 0.05 to 7,
b is from 0.1 to 7,
c is from 0.01 to 5,
d is from 0.1 to 12,
e is from 0 to 5,
f is from 0 to 5,
g is from 0 to 0.2,
h is from 0 to 5, and
x is the number of oxygen atoms required to satisfy the valence requirements of the other component elements present;

wherein a heat-decomposable nitrogen containing compound is added during the preparation of the catalyst.

The process for the preparation of the catalyst typically comprises:

(a) combining source compounds of the metals which comprise the metal oxide catalyst to form a catalyst precursor, (b) drying the catalyst precursor to form catalyst particles, and (c) calcining the catalyst particles to yield the catalyst, The heat-decomposable nitrogen containing compound is added during the process for the preparation of the catalyst prior to the calcination step. In one embodiment, the heat-decomposable nitrogen containing compound is added during the preparation of the catalyst precursor. In one embodiment, the heat-decomposable nitrogen containing compound is added to the catalyst precursor prior to spray drying. In another embodiment, the heat-decomposable nitrogen containing compound is added to the catalyst particles prior to calcination.

The present invention is also directed to processes for the conversion of an olefin selected from the group consisting of propylene and isobutylene or mixtures thereof, to acrylonitrile, and/or methacrylonitrile, and other by-product nitriles (i.e. compounds having the function group "—CN", such acetonitrile and hydrogen cyanide) and mixtures thereof, by reacting in the vapor phase at an elevated temperature and pressure said olefin with a molecular oxygen containing gas and ammonia in the presence of a mixed metal oxide catalyst, wherein the catalyst is prepared as described herein.

DETAILED DESCRIPTION OF THE INVENTION

The instant invention is the preparation of a mixed metal oxide catalyst for the catalytic ammoxidation of propylene, isobutylene or mixtures thereof, to acrylonitrile, methacrylonitrile and mixtures thereof, respectively and for the catalytic oxidation of propylene, isobutylene or mixtures thereof, to acrolein/acrylic acid, methacrolein/methacrylic acid and mixtures thereof, respectively. During the process for the preparation of the catalyst, at least one heat-decomposable nitrogen containing compound is added.

In one embodiment the process for the preparation of the catalyst comprises:
(a) combining source compounds of the metals which comprise the mixed metal oxide catalyst to form a catalyst precursor,
(b) drying the catalyst precursor to form catalyst particles, and
(c) calcining the catalyst particles to yield the catalyst,
wherein at least one heat-decomposable nitrogen containing compound is added during the preparation of the catalyst.

The heat-decomposable nitrogen containing compound is added during the process for the preparation of the catalyst prior to the calcination step. In one embodiment, the heat-decomposable nitrogen containing compound is added during the preparation of the catalyst precursor. In one embodiment, the heat-decomposable nitrogen containing compound is added to the catalyst precursor prior to spray drying. In another embodiment, the heat-decomposable nitrogen containing compound is added to the catalyst particles prior to calcination.

In one embodiment, the process for the preparation of the catalyst comprises:
(a) combining source compounds of the metals which comprise the metal oxide catalyst to form a catalyst precursor,
(b) spray drying the catalyst precursor to form microspheroidal catalyst particles, and
(c) calcining the microspheroidal catalyst particles to yield the catalyst,
wherein a heat-decomposable nitrogen containing compound is added during the process for the preparation of the catalyst.

When employed in the ammoxidation of propylene, catalysts prepared by the above process (i.e. a preparation process which includes the addition of a heat-decomposable nitrogen containing compound are characterized by a greater overall conversion of the propylene to nitriles (i.e. compounds having the function group "—CN"), such as acrylonitrile, hydrogen cyanide and acetonitrile, compared to similar catalysts prepared without the addition of the heat-decomposable nitrogen containing compound. For any catalyst employed in the ammoxidation of propylene, this result may be quantified by calculating "α" as defined by the following relationship:

$$\alpha = [(\% \text{ AN} + (3 \times \% \text{ HCN}) + (1.5 \times \% \text{ ACN})) \div \% \text{ PC}] \times 100$$

wherein % AN is the Acrylonitrile Yield,
  % HCN is the Hydrogen Cyanide Yield,
  % ACN is the Acetonitrile Yield,
  % PC is the Propylene Conversion, and
  "α" is a measure of "nitrogen insertion" or "nitrogen utilization" (i.e. nitrogen from the ammonia combining with propylene to form compounds having the function group "—CN" during the ammoxidation reaction; as such, the greater the "α", the greater overall conversion of the propylene to acrylonitrile, hydrogen cyanide and acetonitrile).

As used herein, "Acrylonitrile Yield" means the percent molar yield of acrylonitrile (expressed as a number without any percent sign) calculated as follows: (moles of acrylonitrile produced÷the moles of propylene fed to the reactor)×100. "Hydrogen Cyanide Yield" means the percent molar yield of hydrogen cyanide (expressed as a number without any percent sign) calculated as follows: ((moles of hydrogen cyanide produced÷3)÷(the moles of propylene fed to the reactor))×100. "Acetonitrile Yield" means the percent molar yield of acetonitrile (expressed as a number without any percent sign) calculated as follows: ((moles of acetonitrile produced÷1.5)÷(the moles of propylene fed to the reactor))×100. Propylene Conversion means the percent molar conversion of propylene to products and byproducts (expressed as a number without any percent sign) calculated as follows: [(the moles of propylene fed to the reactor minus the moles of propylene exiting the reactor)÷the moles of propylene fed to the reactor]×100.

Lastly, when employed in the ammoxidation of propylene, catalysts prepared by the above process (i.e. a preparation process which includes the addition of a heat-decomposable nitrogen containing compound are characterized by less "ammonia burn" compared to similar catalysts prepared without the addition of the heat-decomposable nitrogen containing compound. In simple terms, the "ammonia burn" is a measure of the ammonia consumed in the reaction which is not accounted for by the amount of nitrogen present in the desired reaction products. A lower ammonia burn is desirable because more of the ammonia reacts to form valuable products (e.g. providing a nitrogen to a nitrile) as opposed to reacting to produce by-products or waste products (e.g. $N_2$, $N_2O$, $NO$ or $NO_2$). "Ammonia burn" is typically denoted as a molar percentage of the amount of ammonia fed to the reaction that reacts but does not produce acrylonitrile, HCN, or acetonitrile; and may be calculated as follows: [1−[(moles of acrylonitrile, HCN, and acetonitrile produced+the moles of ammonia exiting the reactor)÷(the moles of ammonia fed to the reactor)]]×100.

The catalyst of the instant invention are characterized by both a high "α" (i.e. greater than 100) and a low "ammonia burn" (i.e. less than about 15%). In general, both "α" and the "ammonia burn" are a measure of how efficient the catalyst is in utilizing ammonia for the ammoxidation of propylene to acrylonitrile.

The Catalyst:

The present invention is directed to a multi-component mixed metal oxide ammoxidation catalytic composition comprising a complex of catalytic oxides wherein the elements and the relative ratios of the elements in said catalytic composition are represented by the following formula:

$$Mo_{12}Bi_aFe_bA_cD_dE_eF_fG_gCe_hO_x$$

wherein A is at least one element selected from the group consisting of sodium, potassium, rubidium and cesium; and D is at least one element selected from the group consisting of nickel, cobalt, manganese, zinc, magnesium, calcium, strontium, cadmium and barium;

E is at least one element selected from the group consisting of chromium, tungsten, boron, aluminum, gallium, indium, phosphorus, arsenic, and vanadium;

F is at least one element selected from the group consisting of lanthanum, praseodymium, neodymium, samarium, europium, gadolinium, terbium, dysprosium, holmium, erbium, thulium, ytterbium, lutetium, scandium, yttrium, element, titanium, zirconium, hafnium, niobium, tantalum, thallium, silicon, germanium, and lead;

G is at least one element selected from the group consisting of silver, gold, ruthenium, rhodium, palladium, osmium, iridium, platinum and mercury; and a, b, c, d, e, f, g, h and n are, respectively, the atomic ratios of bismuth (Bi), iron (Fe), A, D, E, F, cerium (Ce) and oxygen (O), relative to 12 atoms of molybdenum (Mo), wherein a is from 0.05 to 7,
b is from 0.1 to 7,
c is from 0.01 to 5,
d is from 0.1 to 12,
e is from 0 to 5,
f is from 0 to 5,
g is from 0 to 0.2,
h is from 0 to 5, and
x is the number of oxygen atoms required to satisfy the valence requirements of the other component elements present.

In one embodiment the catalyst contains no tellurium, antimony or selenium. In another embodiment, the components or elements designated by "E" in the above formula may also include tellurium and/or antimony. In one embodiment, h is from 0.01 to 5.

In one embodiment of the above described catalytic composition, $0.15 \leq (a+h)/d \leq 1$. In another embodiment of the above described catalytic composition, $0.8 \leq h/b \leq 5$. In yet another embodiment, the X-ray diffraction pattern of the above identified catalytic composition has X-ray diffraction peaks at 2θ angle 28±0.3 degrees and 2θ angle 26.5±0.3 degrees and if the ratio of the intensity of the most intense x-ray diffraction peak within 2θ angle 28±0.3 degrees to the intensity of most intense x-ray diffraction peak within 2θ angle 26.5±0.3 degrees is defined as X/Y, then X/Y is greater than or equal to 0.7. In other independent embodiments of the above identified catalytic composition: $0.2 \leq (a+h)/d \leq 0.6$; $0.3 \leq (a+h)/d \leq 0.5$; $1 \leq h/b \leq 3$; $1.5 \leq h/b \leq 2$; X/Y is greater than or equal to 0.8; and/or X/Y is greater than or equal to 0.90.

In the embodiment, (where $0.8 \leq h/b \leq 5$), "h/b" represents the ratio of cerium to iron in the catalyst and for any catalyst formulation this ratio is simply the moles of cerium (as represented by the subscript for cerium in the formula) divided by the moles of iron (as represented by the subscript for iron in the formula). It has been discovered that catalysts described by the above formula wherein $0.8 \leq h/b \leq 5$ tend to be stronger in that they have a lower attrition loss as determined by a submerged jet attrition test.

In the embodiment, characterized by the X-ray diffraction pattern of the above identified catalytic composition having X-ray diffraction peaks at 2θ angle 28±0.3 degrees and 2θ angle 26.5±0.3 degrees and if the ratio of the intensity of the most intense x-ray diffraction peak within 2θ angle 28±0.3 degrees to the intensity of most intense x-ray diffraction peak within 2θ angle 26.5±0.3 degrees is defined as X/Y, then X/Y is greater than or equal to 0.7, it has been discovered that such catalysts provide greater overall conversion for the ammoxidation of propylene and/or isobutylene to nitriles (i.e. compounds having the function group "—CN", such as acrylonitrile, methacrylonitrile, acetonitrile and hydrogen cyanide).

As used herein, "catalytic composition" and "catalyst" are synonymous and used interchangeably. As used herein, a "rare earth element" means at least one of lanthanum, cerium, praseodymium, neodymium, promethium, samarium, europium, gadolinium, terbium, dysprosium, holmium, erbium, thulium, ytterbium, scandium and yttrium (while cerium is a rare earth element, it is excluded from this list because cerium is a separately listed component of the catalyst described herein). As used herein, "2θ" is synonymous with "2 theta".

The catalyst of the present invention may be used either supported or unsupported (i.e. the catalyst may comprise a support). Suitable supports are silica, alumina, zirconium, titania, or mixtures thereof. A support typically serves as a binder for the catalyst and results in a stronger (i.e. more attrition resistant) catalyst. However, for commercial applications, an appropriate blend of both the active phase (i.e. the complex of catalytic oxides described above) and the support is crucial to obtain an acceptable activity and hardness (attrition resistance) for the catalyst. Typically, the support comprises between 40 and 60 weight percent of the supported catalyst. In one embodiment of this invention, the support may comprise as little as about 30 weight percent of the supported catalyst. In another embodiment of this invention, the support may comprise as much as about 70 weight percent of the supported catalyst.

In one embodiment the catalyst is supported using a silica sol. Typically, silica sols contain some sodium. In one embodiment, the silica sol contains less than 600 ppm sodium. In another embodiment, the silica sol contains less than 200 ppm sodium. Typically, the average colloidal particle diameter of the silica sol is between about 15 nm and about 50 nm. In one embodiment of this invention, the average colloidal particle diameter of the silica sol is about 10 nm and can be as low as about 4 nm. In another embodiment of this invention, the average colloidal particle diameter of the silica sol is about 100 nm. In another embodiment of this invention, the average colloidal particle diameter of the silica sol is about 20 nm.

Catalyst Preparation:

Except for the addition of a heat-decomposable nitrogen containing compound as describe below, the catalyst may be prepared by any of the numerous methods of catalyst preparation which are known to those of skill in the art. A typical preparation method will begin with the formation of a mixture of water, a molybdenum source compound and a support material (e.g. silica sot). Separately, source compounds of the remaining elements in the catalyst are combined in water to form a second mixture. These two mixtures are then combined with stirring at a slightly elevated temperature (approximately 40° C.) to form a catalyst precursor slurry. The catalyst precursor slurry is then dried and denitrified and then calcined as described below.

In one embodiment, the elements in the above identified catalyst composition are combined together in an aqueous catalyst precursor slurry, the aqueous precursor slurry so obtained is dried to form a catalyst precursor, and the catalyst precursor is calcined to form the catalyst. However, unique to the process of the instant invention is the following:

(i) combining, in an aqueous solution, source compounds of Bi and Ce, and optionally one or more of Na, K, Rb, Cs, Ca, lanthanum, praseodymium, neodymium, samarium, europium, gadolinium, terbium, dysprosium, holmium, erbium, thulium, ytterbium, lutetium, scandium, yttrium, Pb, and W, to form a mixture (i.e. a first mixture), (ii) adding a source compound of molybdenum to the mixture (i.e. the first mixture) to react with the mixture and form a precipitate slurry, and (iii) combining the precipitate slurry with source compounds of the remaining elements and of the remaining molybdenum in the catalyst to form the aqueous catalyst precursor slurry.

As used herein, "source compounds" are compounds which contain and/or provide one or more of the metals for the mixed metal oxide catalyst composition. As used herein, "remaining elements" or "remaining elements in the catalyst" refers to those elements and the quantity of those elements represented by "A", "D", "E", "F" and "G" in the above formula which were not included in the first mixture. In one embodiment, some elements may be a part of both the first and second mixture. Further, as used herein, "remaining molybdenum" or "remaining molybdenum in the catalyst" refers to that quantity of molybdenum required in the finished catalyst which was not present (i.e. not included in the preparation of) in the precipitate slurry. Lastly, the sum of the quantities of molybdenum provided in the source compounds of molybdenum added in (ii) and (iii) is equal to the total quantity of molybdenum present in the catalyst.

In the above catalyst preparation, the source compounds of the remaining elements and of the remaining molybdenum which are combined with the precipitate slurry may be combined in any order or combination of such remaining elements and remaining molybdenum. In one embodiment, a mixture of the source compounds of the remaining elements and of the remaining molybdenum is combined with the precipitate slurry to form the aqueous catalyst precursor slurry. In another embodiment, (i) a mixture of the source compounds of the remaining elements is combined with the precipitate slurry, and (ii) source compounds of the remaining molybdenum are separately added to the precipitate slurry to form the aqueous catalyst precursor slurry. In another embodiment, source compounds of the remaining elements and of the remaining molybdenum are added individually (i.e. one at a time) to the precipitate slurry. In another embodiment, multiple (i.e. more than one) mixtures of source compounds of the remaining elements and of the remaining molybdenum, wherein each mixture contains one or more of the source compounds of the remaining elements or of the remaining molybdenum, are separately added (i.e. one mixture at a time or multiple mixtures added simultaneously) to the precipitate slurry to form the aqueous catalyst precursor slurry. In yet another embodiment, a mixture of source compounds of the remaining elements is combined with a source compound of molybdenum and the resulting mixture is then added to the precipitate slurry to form the catalyst precursor slurry. In yet another embodiment, the support is silica ($SiO_2$) and the silica is combined with a source compound for the remaining molybdenum prior to combining the remaining molybdenum with the precipitate slurry (i.e. the silica and a source compound for the remaining molybdenum are combined to form a mixture and then this mixture is added to the precipitate slurry, individually or in combination with one or more source compounds of the remaining elements).

In the above catalyst preparation, molybdenum is added both in the preparation of the precipitate slurry and in the preparation of the aqueous catalyst precursor slurry. On an atomic level, the minimum amount of molybdenum added to form the precipitate slurry is determined by the following relationship $$Mo=1.5(Bi+Ce)+0.5(Rb+Na+K+Cs)+(Ca)+1.5(\text{sum of the number of atoms of lanthanum, praseodymium, neodymium, samarium, europium, gadolinium, terbium, dysprosium, holmium, erbium, thulium, ytterbium, lutetium, scandium and yttrium})+(Pb)-(W)$$

Wherein in the above relationship "Mo" is the number of atoms of molybdenum to be added to the first mixture, and "Bi", "Ce", "Rb", "Na", "K", "Cs", "Ca", "Pb" and "W" are the number of atoms of bismuth, cerium, rubidium, sodium, potassium, cesium, calcium, lead and tungsten respectively, present in the first mixture.

In the above catalyst preparation, typically, the amount of molybdenum added to the first mixture to form the precipitate slurry is about 20 to 35% of the total molybdenum in the final catalyst. In one embodiment, a source compound for the remaining molybdenum present in the catalyst is added to the mixture of the source compounds of the remaining elements (i.e. the second mixture) prior to the combination of the mixture of the remaining elements with the precipitate slurry to form the catalyst precursor slurry. In other embodiments, a source compound of molybdenum containing the remaining molybdenum present in the catalyst is added to the precipitate slurry either prior to, after or simultaneously with, the mixture of the source compounds of the remaining elements (i.e. the second mixture) in order to form the catalyst precursor slurry.

In the above preparation, source compounds of Bi and Ce, and optionally one or more of Na, K, Rb, Cs, Ca, a rare earth element, Pb and W, are combined in an aqueous solution to form a mixture. In one embodiment, bismuth nitrate and optionally other metal nitrates (i.e. nitrates of Na, K, Rb, Cs, Ca, a rare earth element and/or Pb) are dissolved in an aqueous solution of ceric ammonium nitrate. If tungsten is added, the source compound is typically ammonium paratungstate, $(NH_4)_{10}H_2(W_2O_7)_6$.

Added to the mixture comprising the bismuth and cerium (and optionally one or more of Na, K, Rb, Cs, Ca, a rare earth element, Pb and/or W) is a source compound of molybdenum. In one embodiment this source compound of molybdenum is ammonium heptamolybdate dissolved in water. Upon the addition of the molybdenum source compound to the mixture comprising the bismuth and cerium, a reaction will occur which will result in a precipitate and the resulting mixture is the precipitate slurry.

The precipitate slurry is then combined with a mixture of source compound of the remaining elements of the catalyst and a source compound of molybdenum, to form the aqueous catalyst precursor slurry. The mixture of source compounds of the remaining elements and a source compound of molybdenum may be prepared by combining source compounds of the remaining elements in an aqueous solution (e.g. source compounds are combined in water) and then adding a source compound of molybdenum. In one embodiment this source compound of molybdenum is ammonium heptamolybdate dissolved in water. When combining the precipitate slurry with the remaining elements/molybdenum mixture, the order of addition is not important, i.e. the precipitate slurry may be added to the remaining elements/molybdenum mixture or the remaining elements/molybdenum mixture may be added to the precipitate slurry. The aqueous catalyst precursor slurry is maintained at an elevated temperature.

The amount of aqueous solvent in each of the above described aqueous mixtures and slurries may vary due to the solubilities of the source compounds combined to form the particular mixed metal oxide. The amount of aqueous solvent should at least be sufficient to yield a slurry or mixture of solids and liquids which is able to be stirred.

In any case, the source compounds are preferably combined and/or reacted by a protocol that comprises mixing the source compounds during the combination and/or reaction step. The particular mixing mechanism is not critical, and can include for example, mixing (e.g., stirring or agitating) the components during the reaction by any effective method. Such methods include, for example, agitating the contents of the vessel, for example by shaking, tumbling or oscillating the component-containing vessel. Such methods also include, for example, stirring by using a stirring member located at least partially within the reaction vessel and a driving force coupled to the stirring member or to the reaction vessel to provide relative motion between the stirring member and the reaction vessel. The stirring member can be a shaft-driven and/or shaft-supported stirring member. The driving force can be directly coupled to the stirring member or can be indirectly coupled to the stirring member (e.g., via magnetic coupling). The mixing is generally preferably sufficient to mix the components to allow for efficient reaction between components of the reaction medium to form a more homogeneous reaction medium (e.g., and resulting in a more homogeneous mixed metal oxide precursor) as compared to an unmixed reaction. This results in more efficient consumption of starting materials and in a more uniform mixed metal oxide product. Mixing the precipitate slurry during the reaction step also causes the precipitate to form in solution rather than on the sides of the reaction vessel. More advantageously, having the precipitate form in solution allows for particle growth on all faces of the particle rather than the limited exposed faces when the growth occurs out from the reaction vessel wall.

A source compound of molybdenum may include molybdenum (VI) oxide ($MoO_3$), ammonium heptamolybdate or molybdic acid. The source compound of molybdenum may be introduced from any molybdenum oxide such as dioxide, trioxide, pentoxide or heptaoxide. However, it is preferred that a hydrolyzable or decomposable molybdenum salt be utilized as source compound of molybdenum.

Typical source compounds for bismuth, cerium and the remaining elements of the catalyst are nitrate salts of the metals. Such nitrate salts are readily available and easily soluble. A source compound of bismuth may include an oxide or a salt which upon calcination will yield the oxide. The water soluble salts which are easily dispersed but form stable oxides upon heat treating are preferred. In one embodiment the source compound of bismuth is bismuth nitrate, $Bi(NO_3)_3 \cdot 5H_2O$ A source compound of cerium may include an oxide or a salt which upon calcination will yield the oxide. The water soluble salts which are easily dispersed but form stable oxides upon heat treating are preferred. In one embodiment the source compound of cerium is ceric ammonium nitrate, $(NH_4)_2Ce(NO_3)_6$.

A source compound of iron may be obtained from any compound of iron which, upon calcination will result in the oxide. As with the other elements, water soluble salts are preferred for the ease with which they may be uniformly dispersed within the catalyst. Most preferred is ferric nitrate.

Source compounds for the remaining elements may be derived from any suitable source. For example, cobalt, nickel and magnesium may be introduced into the catalyst using nitrate salts. Additionally, magnesium may be introduced into the catalyst as an insoluble carbonate or hydroxide which upon heat treating results in an oxide. Phosphorus may be introduced in the catalyst as an alkaline metal salt or alkaline earth metal salt or the ammonium salt but is preferably introduced as phosphoric acid.

Source compounds for the alkali components of the catalyst may be introduced into the catalyst as an oxide or as a salt which upon calcination will yield the oxide.

Solvents, in addition to water, may be used to prepare the mixed metal oxides according to the invention include, but are not limited to, alcohols such as methanol, ethanol, propanol, diols (e.g. ethylene glycol, propylene glycol, etc.), organic acids such as acetic acid, as well as other polar solvents known in the art. The metal source compounds are at least partially soluble in the solvent.

As previously noted, the catalyst of the present invention may be used either supported or unsupported (i.e. the catalyst may comprise a support). Suitable supports are silica, alumina, zirconia, titania, or mixtures thereof. The support may be added anytime prior to the catalyst precursor slurry being dried. The support may be added at any time during or after the preparation of any mixture of elements, the precipitate slurry or the catalyst precursor slurry. Further the support need not be added in a single point or step (i.e. the support may be added at multiple points in the preparation. In one embodiment, the support is combined with the other ingredients during the preparation of the aqueous catalyst precursor slurry. In one embodiment, the support is added to the precipitate slurry (i.e. after the precipitate slurry is prepared). In one embodiment, the support is combined with the source compound of molybdenum prior to combining the source compound of molybdenum with source compounds of the remaining elements in the catalyst to form the "second mixture" referred to above.

The catalyst precursor slurry is dried and denitrified (i.e. the removal of nitrates) to yield the catalyst precursor. In one embodiment, the catalyst precursor slurry is dried to form catalyst particles. In one embodiment, the catalyst precursor slurry is spray-dried into microspheroidal catalyst particles. In one embodiment the spray dryer outlet temperature of between 110° C. and 350° C. dryer outlet temperature, preferably between 110° C. and 250° C., most preferably between 110° C. and 180° C. In one embodiment the spray dryer is a co-current flow spray dryer (i.e. the particles are sprayed co-current to the gas flow). In another embodiment the spray dryer is countercurrent flow (i.e. the particles are sprayed countercurrent to the gas flow). In another embodiment the spray dryer is a pressure nozzle type spray dryer. In such spray-drying processes, water-containing solid phase particles are sprayed into contact with hot gas (usually air) so as to vaporize the water. The drying is controlled by the temperature of the gas and the distance the particles travel in contact with the gas. It is generally undesirable to adjust these parameters to achieve too rapid drying as this results in a tendency to form dried skins on the partially dried particles of the solid phase which are subsequently ruptured as water occluded within the particles vaporizes and attempts to escape. By the same token, it is desirable to provide the catalyst in a form having as little occluded water as possible. Therefore, where a fluidized bed reactor is to be used and microspheroidal particles are desired, it is advisable to choose the conditions of spray-drying with a view to achieving complete drying without particle rupture. The dried catalyst material is then heated to remove any remaining nitrates. The denitrification temperature may range from 100° C. to 500° C., preferably 250° C. to 450° C.

Finally, the dried and denitrified catalyst precursor is calcined to form the finished catalyst. In one embodiment, the calcination is effected in air. In another embodiment, the calcination is effected in an inert atmosphere. In one embodiment, the catalyst precursor is calcined in nitrogen. Calcination conditions include temperatures ranging from about 300° C. to about 700° C., more preferably from about 350° C. to about 650° C., and in some embodiments, the calcination may be at about 600° C. In one embodiment, calcination may be completed in multiple stages of increasing temperatures. In one embodiment, a first calcination step is conducted at a temperature in the range of about 300° C. to about 450° C., followed by a second calcination step conducted at a temperature in the range of about 500° C. to about 650° C.

Heat Decomposable Nitrogen Containing Compounds

As used herein a heat decomposable nitrogen containing compound is any nitrogen containing compound that will decompose at or below the calcination temperature of the catalyst. The heat decomposable nitrogen containing compound is not a metal nitrate or metal nitrite added to the catalyst preparation as a source compound for a promoter metal in the catalyst. In one embodiment, the heat decomposable nitrogen containing compound does not contain any metals. In one embodiment, the heat decomposable nitrogen containing compound will release ammonia ($NH_3$.)

Suitable heat decomposable nitrogen compounds are selected from the group consisting of alkyl ammonium, amine compounds, amide compounds, nitro benzoic compounds, and cyclic organo-nitrogen compounds. In one embodiment, the heat-decomposable nitrogen containing compound is ammonium hydroxide or an alkyl ammonium hydroxide. In one embodiment, the heat-decomposable nitrogen containing compound is an ammonium salt selected from the group consisting of ammonium nitrate, ammonium nitrite, mono-, di-, tri- and tetra-alkyl ammonium nitrates, and mono-, di-, tri- and tetra-alkyl ammonium nitrites. In one embodiment, the heat-decomposable nitrogen containing compound is an amine compound selected from the group consisting of mono-, di-, and tri-alkyl amines, mono-, di-, and tri-aryl amines, In one embodiment, the heat-decomposable nitrogen containing compound is an amide compound. In one embodiment, the heat-decomposable nitrogen containing compound is urea. In one embodiment, the heat-decomposable nitrogen containing compound is a nitro benzoic compound. In one embodiment, the heat-decomposable nitrogen containing compound is nitrobenzene. In one embodiment, the heat-decomposable nitrogen containing compound is cyclic organo-nitrogen compound selected from the group consisting of pyridines, pyrroles, pyrrolidines, and piperidines. In one embodiment, the heat-decomposable nitrogen containing compound is hydrazine.

Addition of Heat Decomposable Nitrogen Containing Compounds During Catalyst Preparation A key feature of the instant invention is the addition of at least one heat-decomposable nitrogen containing compound during the process for the preparation of the catalyst prior to a calcination step. This additional may occur at any point in the process where the nitrogen containing compound will not impede the reaction and/or combination of the metals which form the active phase or phases of the catalyst.

The heat-decomposable nitrogen containing compound is added in an amount less than or equal to 0.4 weight of additive per weight of catalyst (i.e. 0<weight of additive per weight of catalyst≤0.4). In one embodiment, the heat-decomposable nitrogen containing compound is added in an amount less than or equal to 0.3 weight of additive per weight of catalyst (i.e. 0<weight of additive per weight of catalyst≤0.3). In one embodiment, the heat-decomposable nitrogen containing compound is added in an amount greater than or equal to 0.01 weight of additive per weight of catalyst. In one embodiment, the heat-decomposable nitrogen containing compound is added in an amount greater than or equal to 0.03 weight of additive per weight of catalyst. In one embodiment, the amount of heat-decomposable nitrogen containing compound that is added is within the following range: 0.025≤weight of additive per weight of catalyst≤0.3. As used in this document, "the weight of additive" is the weight of the additive compound excluding any solution or solvents. As used in this document, "the weight of catalyst" is the weight of the finished catalyst, including the weight of any catalyst support and including the weight of the additive.

The heat-decomposable nitrogen compound may be added to the mixture of source compounds of the metals which form the catalyst slurry. In one embodiment, the heat-decomposable nitrogen compound may be added to a preformed molybdenum-bismuth-cerium oxide containing solution or slurry during the catalyst preparation. In one embodiment, the heat-decomposable nitrogen containing compound is added to the catalyst precursor prior to drying. In one embodiment, the heat-decomposable nitrogen containing compound is added to the catalyst particles formed by drying the catalyst precursor prior to calcination.

In one embodiment, the heat-decomposable nitrogen containing compound is added to the catalyst particles formed by spray drying the catalyst precursor by contacting the catalyst particles with a solution comprising the heat-decomposable nitrogen containing compound to form catalyst particles impregnated with the heat-decomposable nitrogen containing compound, and then drying the catalyst particles impregnated with the heat-decomposable nitrogen containing compound. The solution comprising the heat-decomposable nitrogen containing compound may comprise an aqueous solvent or a non-aqueous solvent or a mixture thereof. The contacting may be done by any incipient wetness impregnation technique or method known in the art, including immersion of the catalyst in the solution comprising the heat-decomposable nitrogen containing compound or spraying the solution comprising heat-decomposable nitrogen containing compound onto the catalyst particles. When the catalyst particles are contacted with the solution comprising the heat-decomposable nitrogen containing compound, the solution is absorbed into the pores of the particles. After contacting the particles are "wet" or "damp" with the solution comprising the heat-decomposable nitrogen containing compound. After contacting or impregnation with solution comprising the heat-decomposable nitrogen containing compound, the wet particles are dried to remove the organic or aqueous solvent employed in the solution comprising the heat-decomposable nitrogen containing compound. The wet catalyst is dried by heating at an elevated temperature for a time sufficient to remove the solvent. In one embodiment the impregnated catalyst is dried in a nitrogen atmosphere. Typically, the wet particles are dried at between 100° C. and 300° C. for between 2 hrs. and 5 hrs. In one embodiment the wet particles are dried at about 200° C. for about 3 hrs.

In one embodiment, the heat-decomposable nitrogen containing compound is added to microspheroidal catalyst particles formed by spray drying the catalyst precursor by contacting the microspheroidal catalyst particles with a solution comprising the heat-decomposable nitrogen containing compound to form microspheroidal catalyst particles impregnated with the heat-decomposable nitrogen containing compound, and then drying the microspheroidal catalyst particles impregnated with the heat-decomposable nitrogen containing compound.

Ammoxidation Process

The catalysts of the instant invention are useful in ammoxidation processes for the conversion of an olefin selected from the group consisting of propylene, isobutylene or mixtures thereof, to acrylonitrile, methacrylonitrile and mixtures thereof, respectively, by reacting in the vapor phase at an elevated temperature and pressure said olefin with a molecular oxygen containing gas and ammonia in the presence of the catalyst. The catalysts of the instant invention are also useful for the ammoxidation of methanol to hydrogen cyanide and the ammoxidation of ethanol to acetonitrile. In one embodiment employing the catalysts described herein, methanol and/or ethanol can be co-fed to a process for the ammoxidation of propylene, isobutylene or mixtures thereof to acrylonitrile, methacrylonitrile or mixtures thereof, in order to increase the production of hydrogen cyanide and/or acetonitrile co-products resulting from such process.

Preferably, the ammoxidation reaction is performed in a fluid bed reactor although other types of reactors such as transport line reactors are envisioned. Fluid bed reactors, for the manufacture of acrylonitrile are well known in the prior art. For example, the reactor design set forth in U.S. Pat. No. 3,230,246, herein incorporated by reference, is suitable.

Conditions for the ammoxidation reaction to occur are also well known in the prior art as evidenced by U.S. Pat. Nos. 5,093,299; 4,863,891; 4,767,878 and 4,503,001; herein incorporated by reference. Typically, the ammoxidation process is performed by contacting propylene or isobutylene in the presence of ammonia and oxygen with a fluid bed catalyst at an elevated temperature to produce the acrylonitrile or methacrylonitrile. Any source of oxygen may be employed. For economic reasons, however, it is preferred to use air. The typical molar ratio of the oxygen to olefin in the feed should range from 0.5:1 to 4:1, preferably from 1:1 to 3:1.

The molar ratio of ammonia to olefin in the feed in the reaction may vary from between 0.5:1 to 2:1. There is really no upper limit for the ammonia-olefin ratio, but there is generally no reason to exceed a ratio of 2:1 for economic reasons. Suitable feed ratios for use with the catalyst of the instant invention for the production of acrylonitrile from propylene are an ammonia to propylene ratio in the range of 0.9:1 to 1.3:1, and air to propylene ratio of 8.0:1 to 12.0:1. The catalyst of the instant invention is able to provide high yields of acrylonitrile at relatively low ammonia to propylene feed ratios of about 1:1 to about 1.05:1. These "low ammonia conditions" help to reduce unreacted ammonia in the reactor effluent, a condition known as "ammonia breakthrough", which subsequently helps to reduce process wastes. Specifically, unreacted ammonia must be removed from the reactor effluent prior to the recovery of the acrylonitrile. Unreacted ammonia is typically removed by contacting the reactor effluent with sulfuric acid to yield ammonium sulfate or by contacting the reactor effluent with acrylic acid to yield ammonium acrylate, which in both cases results in a process waste stream to be treated and/or disposed.

The reaction is carried out at a temperature of between the ranges of about 260° to 600° C., preferred ranges being 310° to 500° C., especially preferred being 350° to 480° C. The contact time, although not critical, is generally in the range of 0.1 to 50 seconds, with preference being to a contact time of 1 to 15 seconds.

The products of reaction may be recovered and purified by any of the methods known to those skilled in the art. One such method involves scrubbing the effluent gases from the reactor with cold water or an appropriate solvent to remove the products of the reaction and then purifying the reaction product by distillation.

The primary utility of the catalyst prepared by the process of the instant invention is for the ammoxidation of propylene to acrylonitrile. Other utilities include the ammoxidation of propane to acrylonitrile, and the ammoxidation of glycerol to acrylonitrile. The catalyst prepared by the process of the instant invention may also be used for the oxidation of propylene to acrolein and/or acrylic acid. Such processes are typically two stage processes, wherein propylene is converted in the presence of a catalyst to primarily acrolein in the first stage and the acrolein is converted in the presence of a catalyst to primarily acrylic acid in the second stage. The catalyst described herein is suitable for use in the first stage for the oxidation of propylene to acrolein.

SPECIFIC EMBODIMENTS

In order to illustrate the instant invention, catalyst prepared in accordance with the instant invention were evaluated and compared under similar reaction conditions to similar catalysts prepared by prior art methods outside the scope of the instant invention. These examples are provided for illustrative purposes only.

Catalysts having the composition of $Ni_4Mg_3Fe_{0.9}Rb_{0.192}Cr_{0.05}Bi_{0.72}Ce_{1.76}Mo_{12.502}O_{50.627}$+50 wt % $SiO_2$ (39 nm) were prepared as follows:

Comparative Example 1

No Additive

Reaction mixture A was prepared by heating 10,309 ml of deionized water to 65° C. and then adding with stirring over 30 minutes ammonium heptamolybdate (9371.5 g) to form a clear colorless solution. Silica sol (41,486 g, 41 wt % silica) was then added with stirring.

Reaction mixture B was prepared by heating 1,829 ml of deionized water to 55° C. and then adding with stirring $Fe(NO_3)_3.9H_2O$ (2,221.9 g), $Ni(NO_3)_2.6H_2O$ (7,107.9 g), $Mg(NO_3)_2.6H_2O$ (4,700.5 g), and $Cr(NO_3)_3.9H_2O$ (122.3 g).

Reaction mixture C1 was prepared by heating 2,264.4 ml of deionized water to 65° C. and then adding with stirring over 30 minutes ammonium heptamolybdate (2,058.6 g) to form a clear colorless solution.

Reaction mixture C2 was prepared by heating 2,264.4 ml of deionized water to 65° C. and then adding with stirring over 30 minutes ammonium heptamolybdate (2,058.6 g) to form a clear colorless solution.

Reaction mixture D1 was prepared by heating 5,896.4 g of 50 wt % aqueous $(NH_4)_2Ce(NO_3)_6$ solution to 55° C. While the solution was stirring and heating, $Bi(NO_3)_3.5H_2O$ (1,067.1 g), and $RbNO_3$ (86.5 g) were sequentially added, resulting in a clear orange solution.

Reaction mixture D2 was prepared by heating 5,896.4 g of 50 wt % aqueous $(NH_4)_2Ce(NO_3)_6$ solution to 55° C. While the solution was stirring and heating, $Bi(NO_3)_3.5H_2O$ (1,067.1 g), and $RbNO_3$ (86.5 g) were sequentially added, resulting in a clear orange solution.

Reaction mixture E was prepared by adding with stirring reaction mixture B to reaction mixture A.

Reaction mixture F1 was prepared by adding reaction mixture C1 to reaction mixture D1. This resulted in precipitation of an orange solid. Stirring was continued for 15 minutes while the temperature was maintained in the 50-55° C. range.

Reaction mixture F2 was prepared by adding reaction mixture C2 to reaction mixture D2. This resulted in precipitation of an orange solid. Stirring was continued for 15 minutes while the temperature was maintained in the 50-55° C. range.

Reaction mixture F1, followed by reaction mixture F2, was then sequentially added to reaction mixture E with stirring.

The combined slurry was allowed to stir for one hour while it cooled to approximately 40° C. It was then homogenized in a blender for 3 minutes at 5000 rpm. The slurry was then spray dried at an inlet/outlet temperature of 325/140° C. The resulting powder was denitrified by heat treating for 1 hour in air at 350° C. and then calcined for 1 hour under a nitrogen/air mix (50%/50% v/v) at 560° C. The resulting calcined powder was then tested as a propylene ammoxidation catalyst.

Example 1

With Additive

Reaction mixture A was prepared by heating 153 ml of deionized water to 65° C. and then adding with stirring over 30 minutes ammonium heptamolybdate (138.8 g) to form a clear colorless solution. Silica sol (609.8 g, 41 wt % silica) was then added with stirring.

Reaction mixture B was prepared by heating 28 ml of deionized water to 55° C. and then adding with stirring $Fe(NO_3)_3.9H_2O$ (32.9 g), $Ni(NO_3)_2.6H_2O$ (105.3 g), $Mg(NO_3)_2.6H_2O$ (69.6 g), and $Cr(NO_3)_3.9H_2O$ (1.81 g).

Reaction mixture C was prepared by heating 68 ml of deionized water to 65° C. and then adding with stirring over 30 minutes ammonium heptamolybdate (60.98 g) to form a clear colorless solution.

Reaction mixture D was prepared by heating 174.6 g of 50 wt % aqueous $(NH_4)_2Ce(NO_3)_6$ solution to 55° C. While the solution was stirring and heating, $Bi(NO_3)_3.5H_2O$ (31.6 g), and $RbNO_3$ (2.56 g) were sequentially added, resulting in a clear orange solution.

Reaction mixture E was prepared by adding with stirring reaction mixture B to reaction mixture A.

Reaction mixture F was prepared by adding reaction mixture C to reaction mixture D. This resulted in precipitation of an orange solid. Stirring was continued for 15 minutes while the temperature was maintained in the 50-55° C. range.

Reaction mixture F was then added to reaction mixture E with stirring. $NH_4NO_3$ (24.4 g) was then added with continued stirring to form the final catalyst precursor slurry.

The slurry was allowed to stir for one hour while it cooled to approximately 40° C. It was then homogenized in a blender for 3 minutes at 5000 rpm. The slurry was then spray dried at an inlet/outlet temperature of 325/140° C. The resulting powder was denitrified by heat treating for 1 hour in air at 425° C. and then calcined for 1 hour in air at 580° C. The resulting calcined powder was then tested as a propylene ammoxidation catalyst.

Example 2

With Additive

Reaction mixture A was prepared by heating 153 ml of deionized water to 65° C. and then adding with stirring over 30 minutes ammonium heptamolybdate (138.8 g) to form a clear colorless solution. Silica sol (609.8 g, 41 wt % silica) was then added with stirring.

Reaction mixture B was prepared by heating 27 ml of deionized water to 55° C. and then adding with stirring $Fe(NO_3)_3.9H_2O$ (32.9 g), $Ni(NO_3)_2.6H_2O$ (105.3 g), $Mg(NO_3)_2.6H_2O$ (69.6 g), and $Cr(NO_3)_3.9H_2O$ (1.81 g).

Reaction mixture C was prepared by heating 67 ml of deionized water to 65° C. and then adding with stirring over 30 minutes ammonium heptamolybdate (60.98 g) to form a clear colorless solution.

Reaction mixture D was prepared by heating 174.7 g of 50 wt % aqueous $(NH_4)_2Ce(NO_3)_6$ solution to 55° C. While the solution was stirring and heating, $Bi(NO_3)_3.5H_2O$ (31.6 g), and $RbNO_3$ (2.56 g) were sequentially added, resulting in a clear orange solution.

Reaction mixture E was prepared by adding with stirring reaction mixture B to reaction mixture A.

Reaction mixture F was prepared by adding reaction mixture C to reaction mixture D. This resulted in precipitation of an orange solid. Stirring was continued for 15 minutes while the temperature was maintained in the 50-55° C. range.

Reaction mixture F was then added to reaction mixture E with stirring. $NH_4NO_3$ (57.4 g) was then added with continued stirring to form the final catalyst precursor slurry.

The slurry was allowed to stir for one hour while it cooled to approximately 40° C. It was then homogenized in a blender for 3 minutes at 5000 rpm. The slurry was then spray dried at an inlet/outlet temperature of 325/140° C. The resulting powder was denitrified by heat treating for 1 hour in air at 325° C. and then calcined in air at 560° C. for 1 hour. The resulting calcined powder was then tested as a propylene ammoxidation catalyst.

Example 3

With Additive

Reaction mixture A was prepared by heating 153 ml of deionized water to 65° C. and then adding with stirring over 30 minutes ammonium heptamolybdate (138.8 g) to form a clear colorless solution. Silica sol (609.8 g, 41 wt % silica) was then added with stirring.

Reaction mixture B was prepared by heating 28 ml of deionized water to 55° C. and then adding with stirring $Fe(NO_3)_3.9H_2O$ (32.9 g), $Ni(NO_3)_2.6H_2O$ (105.3 g), $Mg(NO_3)_2.6H_2O$ (69.6 g), and $Cr(NO_3)_3.9H_2O$ (1.81 g).

Reaction mixture C was prepared by heating 67 ml of deionized water to 65° C. and then adding with stirring over 30 minutes ammonium heptamolybdate (60.99 g) to form a clear colorless solution.

Reaction mixture D was prepared by heating 174.7 g of 50 wt % aqueous $(NH_4)_2Ce(NO_3)_6$ solution to 55° C. While the solution was stirring and heating, $Bi(NO_3)_3.5H_2O$ (31.6 g), and $RbNO_3$ (2.56 g) were sequentially added, resulting in a clear orange solution.

Reaction mixture E was prepared by adding with stirring reaction mixture B to reaction mixture A.

Reaction mixture F was prepared by adding reaction mixture C to reaction mixture D. This resulted in precipitation of an orange solid. Stirring was continued for 15 minutes while the temperature was maintained in the 50-55° C. range.

Reaction mixture F was then added to reaction mixture E with stirring. $NH_4NO_3$ (88.1 g) was then added with continued stirring to form the final catalyst precursor slurry.

The slurry was allowed to stir for one hour while it cooled to approximately 40° C. It was then homogenized in a blender for 3 minutes at 5000 rpm. The slurry was then spray dried at an inlet/outlet temperature of 325/140° C. The resulting powder was denitrified by heat treating for 1 hour in air at 325° C. and then calcined in air at 560° C. for 1 hour. The resulting calcined powder was then tested as a propylene ammoxidation catalyst.

Example 4

With Additive Added by Impregnation

Reaction mixture A was prepared by heating 1364 ml of deionized water to 65° C. and then adding with stirring over 30 minutes ammonium heptamolybdate (1239.6 g) to form a clear colorless solution. Silica sol (5488 g, 41 wt % silica) was then added with stirring.

Reaction mixture B was prepared by heating 242 ml of deionized water to 55° C. and then adding with stirring Fe(NO$_3$)$_3$.9H$_2$O (293.9 g), Ni(NO$_3$)$_2$.6H$_2$O (940.2 g), Mg(NO$_3$)$_2$.6H$_2$O (621.8 g), and Cr(NO$_3$)$_3$.9H$_2$O (16.2 g).

Reaction mixture C was prepared by heating 599 ml of deionized water to 65° C. and then adding with stirring over 30 minutes ammonium heptamolybdate (544.6 g) to form a clear colorless solution.

Reaction mixture D was prepared by heating 1560 g of 50 wt % aqueous (NH$_4$)$_2$Ce(NO$_3$)$_6$ solution to 55° C. While the solution was stirring and heating, Bi(NO$_3$)$_3$'5H$_2$O (282.3 g), and RbNO$_3$ (22.89 g) were sequentially added, resulting in a clear orange solution.

Reaction mixture E was prepared by adding with stirring reaction mixture B to reaction mixture A.

Reaction mixture F was prepared by adding reaction mixture C to reaction mixture D. This resulted in precipitation of an orange solid. Stirring was continued for 15 minutes while the temperature was maintained in the 50-55° C. range.

Reaction mixture F was then added to reaction mixture E with stirring.

The slurry was allowed to stir for one hour while it cooled to approximately 40° C. It was then homogenized in a blender for 3 minutes at 5000 rpm. The slurry was then spray dried at an inlet/outlet temperature of 325/140° C. The resulting powder was denitrified by heat treating for 3 hour in air at 290° C.

An aqueous solution of ammonium nitrate was prepared by dissolving 39.96 g NH$_4$NO$_3$ in deionized water. The solution was allowed to warm to room temperature and diluted to a final volume of 50.00 ml.

To 150.0 g of the heat-treated catalyst, 33.0 ml of the above ammonium nitrate solution was added drop wise in 3 ml increments with mixing and with vigorous agitation following each addition. The resulting powder was subjected to further heat treatment for 1 hour in air at 350° C. and then calcined in air at 560° C. for 1 hour. The resulting calcined powder was then tested as a propylene ammoxidation catalyst.

Catalyst Testing

All catalyst were tested in a bench scale reactor for the ammoxidation of propylene to acrylonitrile. All testing was conducted in a 40cc fluid bed reactor. Propylene was feed into the reactor at a rate of 0.07 WWH (i.e. weight of propylene/weight of catalyst/hour), except for Example 2 where the rate was 0.10 WWH. Pressure inside the reactor was maintained at 10 prig. Reaction temperature was 430° C. Samples of reaction products were collected after several days of testing (between about 140 to about 190 hours on stream). Reactor effluent was collected in bubble-type scrubbers containing cold HCl solution. Off-gas rate was measured with soap film meter, and the off-gas composition was determined at the end of the run with the aid of gas chromatograph fitted with a split column gas analyzer. At the end of the recovery run, the entire scrubber liquid was diluted to approximately 200 grams with distilled water. A weighted amount of 2-butanone was used as internal standard in a ~50 gram aliquot of the dilute solution. A 2 μl sample was analyzed in a GC fitted with a flame ionization detector and a Carbowax™ column. The amount of NH$_3$ was determined by titrating the free HCl excess with NaOH solution.

TABLE 1

| Ex. No. | Weight Ammonium Nitrate per Weight of Catalyst | % C$_3^-$ Conv | % AN Yield | % HCN Yield | % Aceto Yield | % NH$_3$ Burn | α |
|---|---|---|---|---|---|---|---|
| C1 | 0 | 98.3 | 83.7 | 3.7 | 1.9 | 19.0 | 99.3 |
| 1 | 0.049 | 98.2 | 82.9 | 4.7 | 1.7 | 11.2 | 101.4 |
| 2 | 0.115 | 98.4 | 81.5 | 5.4 | 1.8 | 9.7 | 102.0 |
| 3 | 0.176 | 98.8 | 82.7 | 5.1 | 2.0 | 7.7 | 102.2 |
| 4 | 0.176 | 98.5 | 85.1 | 3.9 | 2.1 | 13.2 | 101.5 |

Notes:
1. "wwh" is weight of propylene per weight of catalyst per hour in the feed
2. "% C$_3^-$ Conv" is the Propylene Conversion.
3. "% AN Yield" is the Acrylonitrile Yield.
4. "% HCN Yield" is the Hydrogen Cyanide Yield
5. "% Aceto Yield" is the Acetonitrile Yield
6. "α" is calculated as follows: α = [(% AN + (3 × % HCN) + (1.5 × % ACN)) ÷ % PC] × 100
7. "% NH$_3$ burn" is the calculated amount of ammonia in the feed that reacts but does not produce acrylonitrile, HCN, or acetonitrile.
8. Propylene ammoxidation catalysts are typically described on an "Mo$_{12}$" basis (i.e. the subscript of Mo = 12), to convert the compositions to the "Mo$_{12}$" basis, simply divide each subscript in the composition by the shown Mo subscript and then multiply by 12.

The data in Table 1 clearly show the benefit of the present invention. Specifically, catalysts (Examples 1, 2, 3 and 4) prepared with the addition of a heat-decomposable nitrogen containing compound have improved ammonia utilization efficiency as shown by the increased values for α and reduced amount of ammonia burn, compared to a similar catalyst (Example C1) prepared without the addition of the heat-decomposable nitrogen containing compound.

While the foregoing description and the above embodiments are typical for the practice of the instant invention, it is evident that many alternatives, modifications, and variations will be apparent to those skilled in the art in light of this description. Accordingly, it is intended that all such alternatives, modifications and variations are embraced by and fall within the spirit and broad scope of the appended claims.

The claimed invention is:

1. A process for preparation of a catalyst, said catalyst comprising a complex of metal oxides wherein relative ratios of elements in said catalyst are represented by the following formula:

$$Mo_{12}Bi_aFe_bA_cD_dE_eF_fG_gCe_hO_x$$

wherein A is at least one element selected from the group consisting of sodium, potassium, rubidium and cesium;
  D is at least one element selected from the group consisting of nickel, cobalt, manganese, zinc, magnesium, calcium, strontium, cadmium and barium;
  E is at least one element selected from the group consisting of chromium, tungsten, boron, aluminum, gallium, indium, phosphorus, arsenic, and vanadium;
  F is at least one element selected from the group consisting of lanthanum, praseodymium, neodymium, samarium, europium, gadolinium, terbium, dysprosium, holmium, erbium, thulium, ytterbium, lutetium, scandium, yttrium, titanium, zirconium, hafnium, niobium, tantalum, aluminum, gallium, indium, thallium, silicon, germanium, and lead;
  G is at least one element selected from the group consisting of silver, gold, ruthenium, rhodium, palladium, osmium, iridium, platinum and mercury; and
  a is from 0.05 to 7,
  b is from 0.1 to 7,
  c is from 0.01 to 5,
  d is from 0.1 to 12,
  e is from 0 to 5,
  f is from 0 to 5, g is from 0 to 0.2, h is from 0 to 5, and x is the number of oxygen atoms required to satisfy the valence requirements of the other component elements present;

wherein at least one heat-decomposable nitrogen-containing compound is added during the preparation of the catalyst and wherein the heat-decomposable nitrogen-containing compound is selected from the group consisting of ammonium compounds, nitrate compounds, nitrite compounds, amide compounds, nitro benzoic compounds, and ammonium hydroxide compounds.

2. The process of claim 1, wherein the process for the preparation of the catalyst comprises:
   (a) combining source compounds of metals which comprise the catalyst to form a catalyst precursor,
   (b) drying the catalyst precursor to form catalyst particles, and
   (c) calcining the catalyst particles to yield the catalyst.

3. The process of claim 2, wherein the heat-decomposable nitrogen-containing compound is added to the catalyst precursor prior to drying.

4. The process of claim 2, wherein a heat-decomposable nitrogen-containing compound is added to the catalyst particles prior to calcination.

5. The process of claim 4, wherein a heat-decomposable nitrogen-containing compound is added to the catalyst particles by contacting the catalyst particles with a solution comprising the heat-decomposable nitrogen-containing compound to form catalyst particles impregnated with the heat-decomposable nitrogen containing compound.

6. The process of claim 2, wherein the catalyst particles are calcined in nitrogen.

7. The process of claim 2, wherein the catalyst precursor is spray-dried to form microspheroidal catalyst particles.

8. The process of claim 1, wherein the heat-decomposable nitrogen-containing compound is added in an amount in the range of 0<weight of additive per weight of catalyst≤0.4.

9. The process of claim 8, wherein the heat-decomposable nitrogen-containing compound is added in an amount in the range of 0.025<weight of additive per weight of catalyst≤0.3.

10. The process of claim 1, wherein the heat-decomposable nitrogen-containing nitrogen containing compound is selected from the group consisting of alkyl ammonium compounds and alkyl ammonium hydroxide compounds.

11. The process of claim 1, wherein the heat-decomposable nitrogen-containing compound is a nitrate compound selected from the group consisting of ammonium nitrate, and mono-, di-, tri- and tetra-alkyl ammonium nitrates.

12. The process of claim 1, wherein the heat-decomposable nitrogen-containing nitrogen containing compound is a nitrite compound selected from the group consisting of ammonium nitrite, and mono-, di-, and tri-alkyl ammonium nitrites.

13. The process of claim 1, wherein the heat-decomposable nitrogen-containing compound is urea.

14. The process of claim 1, wherein the heat-decomposable nitrogen-containing compound is nitrobenzene.

15. A process for preparation of a catalyst, said catalyst comprising a complex of metal oxides wherein relative ratios of elements in said catalyst are represented by the following formula:

wherein A is at least one element selected from the group consisting of sodium, potassium, rubidium and cesium;

D is at least one element selected from the group consisting of nickel, cobalt, manganese, zinc, magnesium, calcium, strontium, cadmium and barium;

E is at least one element selected from the group consisting of chromium, tungsten, boron, aluminum, gallium, indium, phosphorus, arsenic, antimony, vanadium and tellurium;

F is at least one element selected from the group consisting of lanthanum, praseodymium, neodymium, samarium, europium, gadolinium, terbium, dysprosium, holmium, erbium, thulium, ytterbium, lutetium, scandium, yttrium, titanium, zirconium, hafnium, niobium, tantalum, aluminum, gallium, indium, thallium, silicon, germanium, and lead;

G is at least one element selected from the group consisting of silver, gold, ruthenium, rhodium, palladium, osmium, iridium, platinum and mercury; and a is from 0.05 to 7, b is from 0.1 to 7, c is from 0.01 to 5, d is from 0.1 to 12, e is from 0 to 5, f is from 0 to 5, g is from 0 to 0.2, h is from 0 to 5, and x is the number of oxygen atoms required to satisfy the valence requirements of the other component elements present;

wherein at least one heat-decomposable nitrogen-containing compound is added during the preparation of the catalyst and wherein the heat-decomposable nitrogen-containing compound is selected from the group consisting of ammonium compounds, nitrate compounds, nitrite compounds, amide compounds, nitro benzoic compounds, and ammonium hydroxide compounds.

* * * * *